(12) United States Patent
Riley et al.

(10) Patent No.: US 9,402,864 B2
(45) Date of Patent: Aug. 2, 2016

(54) ORAL IRON DEFICIENCY THERAPY

(75) Inventors: Gary M. Riley, Roseland, NJ (US);
Parshuram Rath, Yorktown Heights, NY (US); Michael Novinski, Long Valley, NJ (US)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 0 days.

(21) Appl. No.: 13/703,283

(22) PCT Filed: Jun. 9, 2011

(86) PCT No.: PCT/US2011/039737
§ 371 (c)(1),
(2), (4) Date: May 20, 2013

(87) PCT Pub. No.: WO2011/156563
PCT Pub. Date: Dec. 15, 2011

(65) Prior Publication Data
US 2013/0230604 A1    Sep. 5, 2013

Related U.S. Application Data

(60) Provisional application No. 61/353,146, filed on Jun. 9, 2010.

(51) Int. Cl.
*A61K 33/26* (2006.01)
*A61K 31/295* (2006.01)

(52) U.S. Cl.
CPC ............... *A61K 33/26* (2013.01); *A61K 31/295* (2013.01)

(58) Field of Classification Search
CPC ........................... A61K 33/26; A61K 31/295
See application file for complete search history.

(56) References Cited

U.S. PATENT DOCUMENTS

| 7,384,982 | B2* | 6/2008 | Bay et al. ............... 514/563 |
| 2004/0072796 | A1* | 4/2004 | Embury et al. ............ 514/56 |
| 2005/0163849 | A1 | 7/2005 | Wong et al. |
| 2007/0065521 | A1 | 3/2007 | Venkataraman et al. |
| 2008/0200380 | A1 | 8/2008 | Lee et al. |

FOREIGN PATENT DOCUMENTS

| EP | 1652527 A1 | 5/2006 |
| GB | 2212396 A | 7/1989 |
| WO | WO-0245754 A2 | 6/2002 |
| WO | WO-2004104018 A2 | 12/2004 |
| WO | WO-2006118948 A2 | 11/2006 |
| WO | WO-2012094598 A2 | 7/2012 |
| WO | WO-2012097155 A1 | 7/2012 |

OTHER PUBLICATIONS

Hörl, "Clinical Aspects of Iron use in the Anemia of Kidney Disease", Frontiers in Nephrology 18: pp. 382-393 (2007).*
Simpson, et al., Transport of Fe 2+ Across Lipid Bilayers Role of Free Fatty Acids, Biochemical et Biophysica Acta, 1987, vol. 898, pp. 187-195.
Public Chemical Database (PubChem) Jul. 21, 2009, CID 43536055.
International Search Report issued in PCT/US11/39737 on Nov. 23, 2011.
Heinrich, et al., Effects of So-Called Iron Absorption-promoting Additives in Humans as Measured with the 59 Fe-absorption Whole-body Retention Test, Intraindividual Comparison of Succinate Dioctylsulfosuccinate-, Fumarate-aspartate, Ardzneimittel Forchung. Drug Research, 1972, 22:7:1091-1103.
European Search Report issued in EP11793140 on Jul. 1, 2014.

* cited by examiner

*Primary Examiner* — Ernst V Arnold
*Assistant Examiner* — Kyung Sook Chang
(74) *Attorney, Agent, or Firm* — Blank Rome LLP

(57) ABSTRACT

Methods of normalizing iron levels, treating iron deficiency and disorders related thereto, such as anemia, as described. Pharmaceutical compositions effective for such treatments are also described.

22 Claims, No Drawings

ORAL IRON DEFICIENCY THERAPY

This application is the U.S. national phase of International Patent Application No. PCT/US2011/039737, filed Jun. 9, 2011, which claims the benefit of U.S. Patent Application No. 61/353,146, filed Jun. 9, 2010, which is incorporated by reference in its entirety.

FIELD OF THE INVENTION

This disclosure relates generally to methods of normalizing iron levels, treating iron deficiency and disorders related thereto, such as anemia. This disclosure also relates to pharmaceutical compositions effective for such treatments.

BACKGROUND OF THE INVENTION

Iron deficiency anemia is a common pathological manifestation in patients with chronic kidney disease (CKD) and is associated with significant increase in cardiac morbidity and mortality (see, e.g., Harnett et al., *Am. J. Kidney Dis.*, 25, S3-S7, 1995; Xue et al., *Am. J. Kidney Dis.*, 40, 1153-1161, 2002; Abramson et al., *Kidney Int.*, 64, 610-615, 2003). Primary causes of anemia in CKD patients are iron deficiency and insufficient erythropoiesis (see, e.g., Eschbach, *Kidney Int.*, 35, 134-148, 1989; Fishbane et al., *Am. J. Kidney Dis.*, 29, 319-333, 1997). Iron deficiency may occur when body iron stores are depleted in CKD patients undergoing hemodialysis due to excess loss of blood. Iron deficiency may also occur due to inflammation induced low mucosal oral iron absorption and decreased mucosal iron transfer in CKD patients undergoing hemodialysis (see e.g., Kooistra et al., *Nephrol. Dial. Transplant.*, 13, 82-88, 1998). Demand for iron is also increased in the production of red blood cells in response to the treatment with erythropoiesis stimulating agents (ESA) in CKD patients. Thus, iron deficiency is an inevitable consequence in patients undergoing hemodialysis and ESA treatment. Correcting iron deficiency is a necessary step for the treatment of anemia in CKD patients (see e.g., Silverberg et al., *Kidney Int. Suppl.*, 69, S79-S85, 1999; Spinowitz et al., *J. Am. Soc. Nephrol.*, 19, 1599-1605, 2008).

The oral iron absorption process occurs in two steps: (1) absorption of iron in the gut by the epithelial cells, and (2) transport of iron from the cells to the systemic circulation. In the first step, oral iron is absorbed and taken up by enterocytes in the proximal duodenum via the epithelial divalent metal ion transporter DMT1 (or DCT1) (see e.g., Gunshin et al., *Nature*, 388(6641), 482-488, 1997). Oral iron in the gut is first converted from $Fe^{3+}$ to $Fe^{2+}$ by a ferri-reductase enzyme and then binds to DMT1 for its transport into the epithelial cells. (2) In the second step, intracellular iron is either taken up by the ubiquitous iron protein ferritin and stored in the cytoplasm, or is transported into the circulation via the basolateral cell surface transporter ferroportin (see, e.g., Abboud et al., *J. Biol. Chem.*, 275(26), 19906-19912, 2000; Donovan et al., *Nature*. 403(6771), 776-781, 2000). Release of iron to the circulation is tightly regulated by the peptide hepcidin secreted by liver. Hepcidin binds to ferroportin thereby initiating ferroportin endocytosis and lysosomal degradation (see, e.g., Nemeth et al., *Science,* 306(5704), 2090-3, 2004). Thus high expression of hepcidin lowers the distribution of ferroportin in the basolateral membrane thereby reducing the release of iron from the duodenal mucosal cells into the circulation.

The bioavailability of oral iron is limited by both the absorption efficiency of the enterocytes and hepcidin regulated release of iron from the mucosal cells. Although oral iron bioavailability was found to be approximately 22% in healthy subjects (see, e.g., Hansen et al., *Phys. Med. Biol.,* 37(6), 1349-1357, 1992) this value will be significantly lower if the absorption and release of iron from the enterocytes is inhibited. Inflammatory cytokine IL-6, a product of macrophages activated by inflammation, is believed to upregulate hepcidin synthesis thereby limiting the release of intracellular iron (see, e.g., Nemeth et al., *J. Clin. Invest.,* 113(9):1271-1276, 2004). Correlation between inflammatory cytokine IL-6 and poor oral iron absorption (reduced more than 60% based on serum iron AUC value) has been observed in patients suffering from Crohn's disease (see, e.g., Semrin et al., *Inflamm. Bowel Dis.,* 12(12), 1101-1106, 2006). Inflammation is prevalent in CKD patients (see, e.g., Oberg et al., *Kidney Int.,* 65(3), 1009-1016, 2004) and bioavailability of conventional oral iron formulation is severely affected primarily through the activation of inflammation-hepcidin pathway described above. Intravenous (IV) iron therapy, however, is effective in dialysis patients as it is able to circumvent the inflammation-hepcidin regulatory pathway by delivering iron directly to the circulation.

Current methods of oral iron therapy typically suffer from low bioavailability of the iron, making them ineffective for the treatment of anemia in CKD patients (see, e.g., Van Wyck et al., *Kidney Int.,* 68, 2846-2856, 2005; Charytan et al., *Nephron. Clin. Pract.,* 100, c55-c62, 2005). Thus, the National Kidney Foundation-Kidney Disease Outcomes Quality Initiative (NKF-KDOQI) has recommended the use of IV iron therapy as the primary means of correcting anemia in dialysis patients (see, e.g., NKF-KDOQI Clinical Practice Guidelines and Clinical Practice Recommendations for Anemia in Chronic Kidney Disease, 2007 update, www.guideline.gov (National Guideline Clearinghouse)). Anemia, however, is not limited to patients with CKD. Inflammation of the stomach lining such as in gastritis, or celiac disease, and any other abnormalities in the metal ion transporters responsible for iron transport renders oral iron absorption insufficient leading to anemia.

Thus, there is a continuing need to develop effective and well-tolerated oral treatments for patients with iron deficiency (for instance, anemic patients with CKD).

BRIEF SUMMARY OF THE INVENTION

The present inventors have developed new formulations for oral administration of iron that may be used as an effective therapy for the treatment of iron deficiency and disorders resulting from iron deficiency, such as anemia, for example, patients with CKD. The present formulations may provide an improved pharmacokinetic profile (e.g., enhanced extent and rate of absorption) when compared to conventional oral formulations. The application of this technology may be useful in reducing the GI discomfort and improving the safety because of the lower dose required due to enhancement of the bioavailability of iron. Moreover, the present formulations may act as an alternative to the current practice of IV iron therapy and thereby result in significant healthcare cost savings.

In one aspect, the present invention relates to a method of normalizing iron levels in a subject with iron deficiency by administering one or more oral dosage forms comprising a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)) and an iron compound.

In another aspect, the present invention relates to a method of improving the response rate of subjects to oral treatment with iron by administering one or more oral dosage forms comprising a delivery agent (e.g., N-[8-(2-hydroxybenzoyl) amino]caprylic acid (NAC) or a pharmaceutically acceptable salt thereof (such as monosodium N-[8-(2-hydroxybenzoyl) amino]caprylic acid (SNAC)) and an iron compound.

In yet another aspect, the present invention relates to a method of treating iron deficiency in a subject by administering one or more oral dosage forms comprising a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)) and an iron compound.

In yet another aspect, the present invention relates to a method of treating anemia in a subject by administering one or more oral dosage forms comprising a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)) and an iron compound.

In certain embodiments, the subject has chronic kidney disease. In other embodiments, the subject is undergoing dialysis. In further embodiments, the subject has Crohn's disease or IBD (Inflammatory Bowel Disease). In additional embodiments, the subject has cancer. In further embodiments, the subject has a gastric disorder (for example, inflammation of the stomach lining, such as in gastritis or Celiac disease). In one embodiment, the subject has autoimmune gastritis. In another embodiment, the subject has *Helicobacter pylori* gastritis. In one embodiment, the gastric disorder decreases nutrient absorption, resulting in insufficient absorption of the nutrient (e.g., iron).

In yet another aspect, the present invention relates to a pharmaceutical composition comprising (a) an iron compound and (b) a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)).

In yet another aspect, the present invention relates to a pharmaceutical composition comprising (a) an iron compound and (b) a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)) wherein the composition forms less than about 5% (e.g., less than 1%) by weight of an iron salt of the delivery agent (based on the total weight of the iron compound and the delivery agent in the initial pharmaceutical composition) after storage for 3 months at 25° C. and 60% relative humidity.

The pharmaceutical composition may further include one or more chelating complexing, or solubilizing agents, and/or anti-oxidants. The pharmaceutical composition may be an oral dosage unit form, such as a tablet or capsule. This pharmaceutical composition can be used in any of the aforementioned methods.

DETAILED DESCRIPTION OF THE INVENTION

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean plus or minus a range of up to 20%, preferably up to 10%, more preferably up to 5%.

As used herein, the term "SNAC" refers to sodium N-[8-(2-hydroxybenzoyl)amino]caprylic acid. SNAC is also known as sodium-N-salicyloyl-8-aminocaprylate, monosodium 8-(N-salicyloylamino) octanoate, N-(salicyloyl)-8-aminooctanoic acid monosodium salt, monosodium N-{8-(2 phenoxybenzoyl)amino}octanoate, E414 monosodium salt, sodium 8-[(2-hydroxybenzoyl)amino]octanoate and salcaprozate. SNAC has the structure:

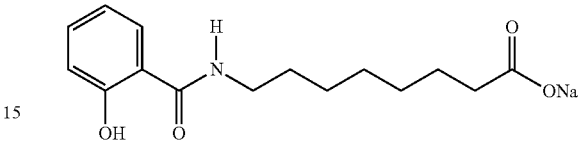

In additional embodiments of any of the methods described herein, NAC or other pharmaceutically salts of SNAC can be used in lieu of SNAC. For example, a disodium salt of NAC, as described in U.S. Pat. No. 7,384,982, may be used. Additionally, any solid state form of SNAC may be used. Suitable solid state forms of SNAC are described, for example, in U.S. Patent Publication No. 2009/0143330, which is hereby incorporated by reference.

In additional embodiments of any of the methods described herein, delivery agents other than SNAC (and its free acid or other pharmaceutically acceptable salts thereof) may be used in combination with an iron compound. Such delivery agents may either be combined with or used in lieu of NAC or its pharmaceutically acceptable salts. Examples of such delivery agents include, but are not limited to, N-(10-[2-hydroxybenzoyl]amino)decanoic acid (the free acid of SNAD), N-(8-[2-hydroxy-5-chlorobenzoyl]-amino)octanoic acid (5-CNAC), 4-[(2-hydroxy-4-chloro-benzoyl)-amino]butanoic acid (4-CNAB), 8-(2-hydroxyphenoxy)octyldiethanolamine (HPOD), 8-(N-2-hydroxy-4-methoxybenzoyl)-aminocaprylic acid (4-MOAC), 3-toluoxybutanoic acid (3-TBA) and pharmaceutically salts thereof (e.g., monosodium and disodium salts thereof). The term "SNAD" refers to the monosodium salt of N-(10-[2-hydroxybenzoyl-]amino)decanoic acid. Other suitable delivery agents are described, for example, in International Publication Nos. WO 96/30036, WO 98/34632, and WO 2007/121318 and U.S. Pat. Nos. 5,650,386, 5,773,647, and 5,866,536, all of which are hereby incorporated by reference.

The term "iron compound" refers to any member of a group of iron-containing compounds, which includes, but is not limited to, iron compounds in which the iron is in the +2 and/or +3 oxidation sate. For example, the iron compound may be ferrous sulphate (and its hydrates), ferrous fumarate, iron dextran, iron gluconate (ferric gluconate), iron sucrose, iron oxide, ferumoxytol, and any combination of any of the foregoing. In one embodiment, the iron present in the iron compound is in the +2 oxidation state. In one embodiment, the iron compound is ferrous sulfate or a hydrate thereof (e.g., ferrous sulfate heptahydrate).

In one embodiment, ion exchange between the iron compound and the delivery agent that results in the formation of an iron salt of the delivery agent is to be minimized. For example, a pharmaceutical composition comprising the iron compound and delivery agent forms less than about 5%, less than about 4%, less than about 3%, less than about 2%, less than about 1%, less than about 0.5%, or less than about 0.2% by weight of an iron salt of the delivery agent (based on the total weight of the iron compound and the delivery agent in the initial pharmaceutical composition), for example, after storage for 1, 2, or 3 months at 25° C. and 60% relative humidity.

In another embodiment, less than about 5%, less than about 4%, less than about 3%, less than about 2%, less than about 1%, less than about 0.5% or less than about 0.2% by weight of the delivery agent in the pharmaceutical composition is in the form of an iron salt.

In further embodiments, pharmaceutical compositions for use in any of the methods described herein may include one or more additional compounds that increase the solubility of the iron compound. Suitable additional compounds include, but are not limited to, compounds that chelate to the iron compound (chelating agents), such as citric acid, complexation agents (cyclodextrins), or solubilizing agents (surfactants). Suitable formulation methods to increase the solubility include, but are not limited to, the use of micronized material or the use of the amorphous form (spray drying/freeze drying)

In further embodiments, pharmaceutical compositions for use in any of the methods described herein may include one or more additional compounds that increase duodenal ferri-reductase activity, thereby aiding in intestinal absorption of iron. Suitable additional compounds include, but are not limited to, ascorbic acid.

In further embodiments, pharmaceutical compositions for use in any of the methods described may herein include one or more antioxidants, such as, but not limited to, ascorbic acid, propyl gallate, and any combination thereof.

In further embodiments, pharmaceutical compositions that may improve bioavailability, such as modified release products using polymers, bilayer (or trilayer) tablets for a more consistent absorption profile, permeation enhancers, extrusion-spheronization to improve the rate of drug/carrier release from the dosage form, may also be used.

For example, in one embodiment, the pharmaceutical composition may be in the form of a bi- or tri-layer tablet having the following structure:

a) a first layer 1 having the property of swelling considerably and quickly on contact with aqueous biological fluids (in one embodiment, the first layer is produced by compression of a mixture or of a granulate comprising hydrophilic polymers constituting from about 5 to 90% (e.g., from about 10 to about 85%) of the weight of the layer);

b) a second layer 2 adjacent to the first layer, in which the iron compound (e.g., ferrous sulphate) and delivery agent (e.g., SNAC) are conveyed (in one embodiment, the second layer is formulated with hydrophilic polymers and with other auxiliary substances, in order to give the preparation suitable properties of compressibility and in order to allow the release of iron compound and delivery agent within a predetermined time period); and c) optionally a third layer 3 obtained by compression and applied to layer 2, (in one embodiment, the third layer contains hydrophilic polymers which gel and/or swell and which may then optionally be broken down and having a barrier function which modifies the release of the iron compound and delivery agent from layer 2, layer 3 being primarily highly impervious to passage of the active substance.

In certain embodiments, on contact with gastric juices, after rapid and considerable swelling of at least one of layers 1 or 3, as well as by the possible swelling of layer 2, the pharmaceutical composition increases considerably in volume; thus, the pharmaceutical preparation remains in the stomach for longer. In this way, most of the iron compound and delivery agent contained may be absorbed in a controlled manner in that portion of the gastrointestinal tract which has the highest capacity for absorption of iron.

In one embodiment, layers 1 and 3 have an identical composition and identical functional properties. In another embodiment, layers 1 and 3 have a different composition and different properties. When the layers 1 and 3 have identical functional properties and compositions, they may differ by their amounts and their thicknesses applied to the layer 2.

In one embodiment, at least one of layers 1 and 3 acts as a barrier that it is primarily highly impervious to passage of the iron compound and delivery agent contained in layer 2 and at least one of the layers is characterized in that it swells quickly, i.e., quickly increases in volume.

In another embodiment, the pharmaceutical composition is a tablet containing 3 layers comprising a first layer 1 as described above, whose function is to increase considerably in volume on contact with aqueous liquids; a second layer 2 conveying some of the iron compound and delivery agent which has to be released within a predetermined time period; and a third layer 3 in which some of the iron compound and delivery agent are conveyed, formulated such that it can be released immediately on contact with gastric juices.

In further embodiments, the polymeric substances which are used in the layers 1 and 3, and which may also be used in the layer 2, are biocompatible and have hydrophilic properties. For example, they are slowly soluble and/or slowly gellable and/or swell rapidly or at a different rate in aqueous liquids and then may optionally be broken down.

Suitable examples of hydrophilic polymers include, but are not limited to, hydroxymethylcellulose, hydroxyethylcellulose, hydroxypropylmethylcellulose having a molecular weight of from about 1000 to about 4,000,000, hydroxypropylcellulose having a molecular weight of from about 2000 to about 2,000,000, carboxyvinyl polymers, chitosans, mannans, galactomannans, xanthans, carrageenans, amylose, alginic acid, its salts and its derivatives, pectins, acrylates, methacrylates, acrylic/methacrylic copolymers, polyanhydrides, polyamino acids, poly(methyl vinyl ether/maleic anhydride) polymers, polyvinyl alcohols, glucans, scleroglucans, carboxymethylcellulose and its derivatives, ethylcellulose, methylcellulose, hydrophilic cellulose derivatives, and combinations thereof.

In one embodiment, the content of hydrophilic polymers ranges from about 5 to about 90% relative to the total weight of the layer, (e.g., from about 10 to about 85%, such as from about 20 to about 80%).

In further embodiments, in order to promote a rapid and considerable increase in the volume of the pharmaceutical preparation, during the preparation of the layers 1 and 3 with the hydrophilic polymers described above, it is possible to use hydrophilic products and/or excipients capable of promoting wetting of the layers, in this way facilitating interaction between the components of the said layer and the biological fluids with which the layer comes into contact. For example, these hydrophilic excipients may include crosslinked polyvinylpyrrolidone, hydroxypropylcellulose and hydroxypropylmethylcellulose having a molecular weight from about 1,000 to about 100,000, crosslinked sodium carboxymethylcellulose, carboxymethyl starch and its salts, divinylbenzene/potassium methacrylate copolymer, and combinations thereof.

In one aspect, the present invention relates to a method of increasing or normalizing iron levels in a subject with low iron levels by administering one or more oral dosage forms comprising a delivery agent (e.g., N-[8-(2-hydroxybenzoyl) amino]caprylic acid (NAC) or a pharmaceutically acceptable salt thereof (such as monosodium N-[8-(2-hydroxybenzoyl) amino]caprylic acid (SNAC)) and an iron compound.

In another aspect, the present invention relates to a method of improving the response rate of subjects to oral treatment with iron by administering to each subject one or more oral dosage forms comprising a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)) and an iron compound. In certain embodiments, the subject suffers from low iron or iron deficiency.

In yet another aspect, the present invention relates to a method of treating iron deficiency in a subject by administering one or more oral dosage forms comprising a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)) and an iron compound.

In yet another aspect, the present invention relates to a method of treating anemia in a subject by administering daily one or more oral dosage forms comprising a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)) and an iron compound.

In certain embodiments, the subject has chronic kidney disease. In other embodiments, the subject is undergoing dialysis. In further embodiments, the subject has Crohn's disease. In additional embodiments, the subject has cancer. In further embodiments, the subject has a gastric disorder (for example, inflammation of the stomach lining, such as in gastritis or Celiac disease). In one embodiment, the subject has autoimmune gastritis. In another embodiment, the subject has *Helicobacter pylori* gastritis. In one embodiment, the gastric disorder decreases nutrient absorption, resulting in insufficient absorption of the nutrient (e.g., iron).

In additional embodiments, any of the methods described herein achieve a patient response rate and/or efficacy similar to that observed for intravenous administration.

In additional embodiments of any of the methods described herein, the one or more dosage forms are administered daily. In additional embodiments of any of the methods described herein, the one or more dosage forms are administered once a week. In additional embodiments of any of the methods described herein, the one or more dosage forms are administered once every two weeks. In additional embodiments of any of the methods described herein, the one or more dosage forms are administered once a month.

The pharmaceutical compositions and dosage forms may further include one or more chelating agents and/or anti-oxidants, as described above.

In yet another aspect, the present invention relates to a pharmaceutical composition comprising (a) an iron compound and (b) a delivery agent (e.g., N-[8-(2-hydroxybenzoyl)amino]caprylic acid (NAC) or a pharmaceutically acceptable salt thereof (such as monosodium N-[8-(2-hydroxybenzoyl)amino]caprylic acid (SNAC)).

The pharmaceutical composition may further include one or more chelating agents and/or anti-oxidants. This pharmaceutical composition can be used in any of the aforementioned methods.

In additional embodiments of any of the methods described herein, the patient can be one who has failed to respond to existing oral iron treatment (or, for instance, oral treatment with an iron containing formulation which does not include a delivery agent, such as SNAC).

In further embodiments of any of the methods described herein, the present invention relates to the administration of a tablet dosage form.

The weight ratio and amount of iron and delivery agent (e.g., SNAC, or other form of NAC) can be as described herein. One of ordinary skill in the art would readily be able to determine the amount of iron present in a formulation based on the amount of a particular iron compound used. For example, 300 mg of ferrous sulfate heptahydrate is equivalent to about 60 mg of iron.

In some embodiments, the oral pharmaceutical composition includes from about 1 to about 1000 mg, from about 1 to about 500 mg, from about 1 to about 300 mg, from about 1 to about 200 mg, from about 5 to about 100 mg, from about 25 to about 500 mg, from about 10 to about 1000 mg, from about 25 to about 250 mg, from about 30 to about 800 mg, from about 50 to about 500 mg, from about 50 to about 250 mg, from about 50 to about 100 mg, from about 100 to about 1000 mg, from about 100 to about 500 mg, from about 250 to about 750 mg, or from about 250 to about 500 mg of iron.

In additional embodiments, the oral pharmaceutical composition includes about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg of iron.

In one embodiment, the oral pharmaceutical composition includes from about 1 mg to about 500 mg of iron and from about 1 mg to about 1000 mg of delivery agent (e.g., SNAC).

In one embodiment, the oral pharmaceutical composition includes from about 5 mg to about 100 mg of iron and from about 50 mg to about 300 mg of delivery agent (e.g., SNAC).

In another embodiment, the oral pharmaceutical composition includes from about 100 mg to about 1000 mg of iron and from about 250 mg to about 10000 mg of delivery agent (e.g., SNAC).

In additional embodiments, the dosage form, such as a tablet dosage form, may contain from about 1 mg to about 500 mg of iron and from about 10 mg to about 600 mg of delivery agent (e.g., SNAC). For example, the dosage form may contain from about 25 mg to about 500 mg of iron or from about 25 mg to about 300 mg of iron or from about 50 mg to about 200 mg of iron and from about 10 mg to about 500 mg of delivery agent (e.g., SNAC), or from about 25 mg to about 400 mg of delivery agent (e.g., SNAC) in each tablet.

In one embodiment, the dosage form, such as a tablet dosage form, contains from about 30 mg to about 150 mg of iron and about 50 mg to about 300 mg of SNAC.

In one embodiment, the dosage form, such as a tablet dosage form includes from about 1 mg to about 200 mg of iron and the dosage form is administered twice a day.

In another embodiment, the dosage form, such as a tablet dosage form includes from about 100 mg to about 1000 mg of iron and the dosage form is administered once a month.

In other embodiments, the weight ratio of iron to delivery agent (e.g., SNAC) is from about 2:1 to about 1:700, such as from about 1:2 to about 1:600, from about 1:2 to about 1:200, from about 1:2 to about 1:100, from about 1:3 to about 1:20 or from about 1:4 to about 1:10. In one embodiment, the weight ratio of iron to of delivery agent (e.g., SNAC) is about 1 to 100.

In other embodiments, the dosage form (e.g., a tablet) optionally contains excipients, emulsifiers, stabilizers, sweeteners, flavoring agents, diluents, coloring agents and/or solubilizing agents, or any combination thereof. Suitable excipients, emulsifiers, stabilizers, sweeteners, flavoring agents, diluents, coloring agents, and solubilizing agents include those described in the *Handbook of Pharmaceutical Excipients* (fourth edition) by Raymond C. Rowe, Paul J. Sheskey and Paul J. Weller.

Exemplary formulations according to the present invention are provided in the tables below. The formulations may contain one or more additional excipients in addition to those identified in the tables.

Exemplary Immediate Release Formulations for Twice Daily Administration

| Ingredient | Amount (mg) | Amount (mg) | Amount (mg) |
| --- | --- | --- | --- |
| SNAC | 1-500 | 20-400 | 50-300 |
| Iron (from an iron compound such as ferrous sulfate) | 1-300 | 1-200 | 5-100 |
| Citric acid | 10-400 | 20-300 | 50-200 |
| Ascorbic acid | 10-400 | 20-300 | 50-200 |
| Propyl gallate | 10-400 | 20-300 | 20-150 |
| Pre-gelatinized starch | 10-500 | 20-200 | 20-150 |
| Microcrystalline cellulose | 1-500 | 1-200 | 2-150 |
| Povidone | 1-100 | 1-75 | 1-50 |
| Dibasic calcium phosphate | 10-500 | 20-200 | 20-150 |

Exemplary Modified Release Formulations for Once Monthly Administration

| Ingredient | Amount (mg) | Amount (mg) | Amount (mg) |
| --- | --- | --- | --- |
| SNAC | 10-5000 | 30-2000 | 50-1000 |
| Iron (from an iron compound such as ferrous sulfate) | 10-1000 | 25-800 | 50-500 |

Exemplary Bi- and Tri-Layer Tablets

| Layer 1 | Layer 2 | Layer 3 (Optional) |
| --- | --- | --- |
| Ingredients | | |
| Hydroxypropyl methylcellulose | Iron compound (e.g., ferrous sulfate) | Hydroxypropyl methylcellulose |
| Hydrogenated castor oil | Delivery agent (e.g., SNAC) | Hydrogenated castor oil |
| Ethyl cellulose | Mannitol | Polyvinylpyrrolidone |
| Magnesium stearate | Hydroxypropyl methylcellulose | Magnesium stearate |
| Silica gel | Polyvinylpyrrolidone Microcrystalline cellulose Magnesium stearate Colloidal silica | Colloidal silica |

Bi- and tri-layer tablets may be prepared by the methods described in U.S. Pat. No. 6,149,940, which is incorporated by reference in its entirety.

Bioavailability of conventional iron formulations depends on the iron uptake efficiency of the diavalent metal transporter DMT1 mediated duodenal mucosal absorption and ferroportin dependent transfer of mucosal iron to the circulation. Without intending to be bound by any particular theory of operation, it is believed that in addition to this normal pathway of oral iron absorption, the oral dosage forms described herein may use an alternate absorption pathway (passive transport) independent of either DMT1 mediated iron uptake or ferroportin mediated iron transfer.

The term "treatment" or "treating" means any treatment of a disease or disorder in a mammal, including: preventing or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms.

A subject or patient in whom administration of the oral pharmaceutical composition is an effective therapeutic regimen for a disease or disorder is preferably a human, but can be any animal, including a laboratory animal in the context of a trial or screening or activity experiment. Thus, as can be readily appreciated by one of ordinary skill in the art, the methods and compositions of the present invention are particularly suited to administration to any animal, particularly a mammal (e.g., a human), and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited.

Example 1

Preparation of N-[8-(2-hydroxybenzoyl)amino]caprylic acid and SNAC

The preparation method for N-[8-(2-hydroxybenzoyl) amino]caprylic acid and SNAC involves the following steps: The starting material is salicylamide, which is converted to form carsalam (1,3-benzoxazine-2,4-dione). The second step involves the alkylation of carsalam. The penultimate step is a hydrolysis to cleave the ethyl protection group at the end of the alkyl chain and open the heterocyclic ring forming the free acid of SNAC. In the final step, the sodium salt of the SNAC free acid is formed by reaction with a 1% excess stoichiometric amount of sodium hydroxide base. Upon cooling the precipitated product is isolated by centrifugation and vacuum dried prior to packaging. The in-process controls for the synthetic scheme are given in Table 1.

TABLE 1

In-process controls for SNAC Manufacturing Process.

| Step | Reaction | Desired Product | Specification | In-Process Control |
| --- | --- | --- | --- | --- |
| 1 | Carsalam | Carsalam | <10% salicylamide | HPLC |

TABLE 1-continued

In-process controls for SNAC Manufacturing Process.

| Step | Reaction | Desired Product | Specification | In-Process Control |
|---|---|---|---|---|
| 2 | Alkylation | Alkylated carsalam | <8% carsalam | HPLC |
| 3 | Hydrolysis | SNAC free acid | <0.5% | LOD |
| 4 | Sodium Salt | SNAC sodium salt | 95-105% | HPLC |

Example 2

A Single Dose Pharmacokinetic Study in Normal Dogs

A single dose pharmacokinetic study in four normal (i.e., non-anemic) dogs will be conducted to test various ferrous sulphate/SNAC containing pharmaceutical compositions according to the present invention. The pharmacokinetic and bioavailability data will be compared with that obtained using a commercial iron supplement therapy formulation (Feosol®, ferrous sulphate tablets). Details of the proposed dog study (Dog Study 1) are shown in Table 1.

TABLE 1

Proposed Formulations For Use In Dog Study 1

| Formulation 1 (Solution) | Formulation 2 (Tablet) | Formulation 3 (Tablet) | Formulation 4 (Tablet) | Formulation 5 (Tablet) | Formulation 6 (Tablet) |
|---|---|---|---|---|---|
| Ferrous sulfate Intravenous | Conventional Ferrous sulfate tablet (Feosol ®) | Ferrous sulfate | Ferrous sulfate | Ferrous sulfate | Ferrous sulfate |
|  |  | SNAC | SNAC Citric acid (chelator) | SNAC Citric acid (chelator) Ascorbic acid (anti oxidant and iron absorption promoter) | SNAC Citric acid (chelator) Ascorbic acid (anti oxidant and iron absorption promoter) Propyl gallate (anti-oxidant) |

Optimization of Composition

The effectiveness of the chelator and anti-oxidant in the formulations will be assessed based on the results of Dog Study 1. For example, if Formulation 3 proves to be the best performing tablet formulation, then it may be necessary only to adjust the SNAC to ferrous sulfate ratio in order to achieve an optimum formulation without the addition of a chelator or anti-oxidant. Alternatively, if Formulation 5 performs the best among all the tablet formulations, then it may be necessary to adjust the amount of ascorbic acid in order to achieve an optimum formulation for oral bioavailability of iron.

Dose Optimization

Based on the results of the Dog Study 1, either Formulation 3 or a variant of Formulation 4, 5, or 6 will be selected for a follow-up study to select the optimum ratio of SNAC and ferrous sulfate to ensure optimum oral absorption. Three ratios of SNAC and ferrous sulfate will be used in a second dog study (Dog Study 2). Suitable SNAC-iron formulations for Dog Study 2 are shown in Table 2 below.

TABLE 2

Proposed Ferrous Sulfate and Escalating SNAC Dose in Normal Dogs (Dog Study 2)

| Formulation 7 (Tablet) | Formulation 8 (Tablet) | Formulation 9 (Tablet) |
|---|---|---|
| Ferrous Sulfate SNAC Dose 1 | Ferrous Sulfate SNAC Dose 2 | Ferrous Sulfate SNAC Dose 3 |

Based on the outcome of Dog study 2, a further optimized SNAC-ferrous sulfate ratio will be selected for future study in an anemic dog model.

Pharmacokinetic and Bioavailability Analysis

In Dog Studies 1 and 2, each dog will be dosed with the selected formulation and blood samples will be collected. Blood samples will be analyzed for total iron content and also for total iron binding capacity (TIBC) for pharmacokinetic analysis and iron status determination.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

The contents of all patents and publications cited herein are hereby incorporated herein by reference in their entireties, to the extent permitted.

What is claimed is:

1. A method of treating iron deficiency in a human patient comprising swallowing one or more immediate release solid oral dosage forms comprising a delivery agent and an iron compound, wherein the weight ratio of iron compound to the delivery agent is from about 2:1 to about 1:700, and wherein the delivery agent is selected from N-[8-(2-hydroxybenzoyl)amino]caprylic acid, N-(10-[2-hydroxybenzoyl]amino)decanoic acid, N-(8-[2-hydroxy-5-chlorobenzoyl]-amino)octanoic acid, 4-[(2-hydroxy-4-chloro-benzoyl)-amino]butanoic acid, 8-(2-hydroxyphenoxy)octyldiethanolamine, 8-(N-2-hydroxy-4-methoxybenzoyl)aminocaprylic acid, 3-toluoxybutanoic acid, and pharmaceutically salts thereof.

2. A method of treating anemia in a human patient comprising swallowing one or more solid oral dosage forms comprising a delivery agent and an iron compound, wherein the weight ratio of iron compound to the delivery agent is from about 2:1 to about 1:700, and wherein the delivery agent is selected from N-[8-(2-hydroxybenzoyl)amino]caprylic acid, N-(10-[2-hydroxybenzoyl]amino)decanoic acid, N-(8-[2-hydroxy-5-chlorobenzoyl]-amino) octanoic acid, 4-[(2-hydroxy-4-chloro-benzoyl)-amino]butanoic acid, 8-(2-hydroxyphenoxy) octyldiethanolamine, 8-(N-2-hydroxy-4-methoxybenzoyl)-aminocaprylic acid, 3-toluoxybutanoic acid, and pharmaceutically salts thereof.

3. The method of claim 1, wherein the delivery agent is N-(8-[2-hydroxy-5-chlorobenzoyl]-amino)octanoic acid, or a pharmaceutically salt thereof.

4. The method of claim 1, wherein the delivery agent is 3-toluoxybutanoic acid, or a pharmaceutically salt thereof.

5. The method of claim 1, wherein the delivery agent is N-(10-[2-hydroxybenzoyl]amino)decanoic acid, or a pharmaceutically salt thereof.

6. The method of claim 1, wherein the delivery agent is 4-[(2-hydroxy-4-chloro-benzoyl)-amino]butanoic acid, or a pharmaceutically salt thereof.

7. The method of claim 1, wherein the delivery agent is 8-(2-hydroxyphenoxy)octyldiethanolamine, or a pharmaceutically salt thereof.

8. The method of claim 1, wherein the delivery agent is 8-(N-2-hydroxy-4-methoxybenzoyl)-aminocaprylic acid, or a pharmaceutically salt thereof.

9. The method of claim 1, wherein the human patient has chronic kidney disease.

10. The method of claim 1, wherein the human patient is undergoing dialysis.

11. The method of claim 1, wherein the human patient has Crohn's disease.

12. The method of claim 1, wherein the human patient has cancer.

13. The method of claim 1, wherein the human patient has gastritis or Celiac disease.

14. The method of claim 1, wherein the dosage form is a tablet.

15. The method of claim 1, wherein the delivery agent is a monosodium salt of N-[8-(2-hydroxybenzoyl)amino]caprylic acid.

16. The method of claim 1, wherein the iron compound is ferrous sulfate, or a hydrate thereof.

17. The method of claim 1, wherein the weight ratio of iron compound to the delivery agent is from about 1:2 to about 1:100.

18. The method of claim 1, wherein the weight ratio of iron compound to the delivery agent is from about 1:3 to about 1:20.

19. The method of claim 1, wherein the weight ratio of iron compound to the delivery agent is from about 1:4 to about 1:10.

20. The method of claim 2, wherein the weight ratio of iron compound to the delivery agent is from about 1:2 to about 1:100.

21. The method of claim 2, wherein the weight ratio of iron compound to the delivery agent is from about 1:3 to about 1:20.

22. The method of claim 2, wherein the weight ratio of iron compound to the delivery agent is from about 1:4 to about 1:10.

* * * * *